(12) United States Patent
Gutmann et al.

(10) Patent No.: US 8,101,606 B2
(45) Date of Patent: Jan. 24, 2012

(54) NEUROFIBROMIN PATHWAY MODULATORS

(75) Inventors: David Gutmann, St. Louis, MO (US); Jason Weber, St. Louis, MO (US)

(73) Assignee: Washington University, St. Louis, MO (US)

( * ) Notice: Subject to any disclaimer, the term of this patent is extended or adjusted under 35 U.S.C. 154(b) by 203 days.

(21) Appl. No.: 12/269,681

(22) Filed: Nov. 12, 2008

(65) Prior Publication Data

US 2009/0208953 A1   Aug. 20, 2009

Related U.S. Application Data

(60) Provisional application No. 60/987,156, filed on Nov. 12, 2007.

(51) Int. Cl.
*A61K 31/5355* (2006.01)
*A61K 31/63* (2006.01)
*A61K 31/695* (2006.01)

(52) U.S. Cl. .................. 514/233.5; 514/600; 514/63

(58) Field of Classification Search .................. None
See application file for complete search history.

(56) References Cited

U.S. PATENT DOCUMENTS

| 4,508,703 | A |   | 4/1985  | Redziniak |         |
|-----------|---|---|---------|-----------|---------|
| 4,621,023 | A |   | 11/1986 | Redziniak |         |
| 5,077,211 | A |   | 12/1991 | Yarosh    |         |
| 7,517,890 | B2| * | 4/2009  | Zheng et al. | 514/275 |

FOREIGN PATENT DOCUMENTS

| WO | 0242265 A2 | 5/2002 |
| WO | 0242276 A1 | 5/2002 |

OTHER PUBLICATIONS

Nakai et al., Journal of Neuroscience, 26(13), (Mar. 29, 2006), pp. 3390-3395.*
Sandsmark et al., Cancer Research, 67(10), (May 15, 2007), pp. 4790-4799.*
Bulinski et al, Overexpression of MAP4 inhibits organelle motility and trafficking in vivo, 1997, J. of Cell Science, pp. 3055-3064, vol. 110.
Clas, Quaternized Colestipol, An Improved Bile Salt Adsorbent: In Vitro Studies, 1991, J. of Pharm. Sci., pp. 128-131, vol. 80, No. 2.
Muhlradt et al, Epothilone B Stabilizes Microtubuli of Macrophages Like Taxol without Showing Taxol-like Endotoxin Activity, 1997, Cancer Res., pp. 3344-3346, vol. 57.
Nicolaou et al, Synthesis of epothilones A and B in solid and solution phase, 1997, Nature, pp. 268-272, vol. 387, No. 6630.
Panda et al, Differential Effects of Vinblastine on Polymerization and Dynamics at Opposite Microtubule Ends, 1996, J. of Biological Chem., pp. 29807-29812, vol. 271, No. 47.
Panda, et al, Stabilization of microtubule dynamics by estramustine by binding to a novel site in tubulin: A possible mechanistic basis for its antitumor action, 1997, PNAS, pp. 10560-10564, vol. 94.
Service, Tumor-Killer Made; How Does It Work?, 1996, Science, pp. 2009, vol. 274, No. 5295.
Vasquez et al, Nanomolar Concentrations of Nocodazole Alter Microtubule Dynamic Instability in Vivo and in Vitro, 1997, Mol. Biol. Cell., pp. 973-985, vol. 8.

\* cited by examiner

*Primary Examiner* — Phyllis G. Spivack
(74) *Attorney, Agent, or Firm* — Polsinelli Shughart PC

(57) ABSTRACT

The present invention encompasses methods for treating neurofibromatosis.

6 Claims, 15 Drawing Sheets
(5 of 15 Drawing Sheet(s) Filed in Color)

NEUROFIBROMIN PATHWAY MODULATORS

CROSS REFERENCE TO RELATED APPLICATIONS

This application claims the priority of U.S. provisional application No. 60/987,156, filed Nov. 12, 2007, which is hereby incorporated by reference in its entirety.

GOVERNMENTAL RIGHTS

This invention was made in part with Government support under Grant Number DAMD-17-03-1-0215 awarded by The Department of Defense and Grant Number U01-CA84314 awarded by the National Cancer Institute. The Government may have certain rights in this invention.

FIELD OF THE INVENTION

The present invention relates to methods for treating neurofibromatosis and to methods for screening for modulators of the neurofibromin pathway.

BACKGROUND OF THE INVENTION

NF1 is a common autosomal dominant disorder that affects approximately 1:3000 people worldwide (over 100,000 individuals in the United States alone) and predisposes to the development of both benign and malignant tumors, including optic glioma and malignant peripheral nerve sheath tumor (MPNST). Optic glioma (astrocytoma) represents the second most common tumor occurring in individuals with NF1. Optic gliomas affect at least 15% of children with NF1, typically in the first decade of life, with 52% of affected children developing signs or symptoms from their tumors. Optic pathway tumors can lead to blindness or invade into nearby brain regions or the subarachnoid space to result in precocious puberty or other neurological abnormalities.

The most commonly used therapy for optic pathway glioma in NF1 is chemotherapy, involving the combination of carboplatin and vincristine. Although initial clinical responses are observed in 60-80% of children with low-grade glioma, tumor progression occurs in 36% of children with optic pathway glioma, necessitating additional therapy. MPNSTs are highly aggressive and malignant tumors composed of neoplastic Schwann cells. Recent studies have shown that MPNSTs are not uncommon cancers in NF1, and affect nearly 10% of individuals with NF1. MPNSTs frequently recur after treatment, and often metastasize to lung and other organs. Current treatment is wide local excision followed by local radiation. However, 5-year survival rates are dismal, and no effective chemotherapy regimens are available. In addition, mean survival appears to be worse in NF1 subjects with MPNST than for those in the general population.

There is an unmet need in the art for more effective treatment of these tumors. New treatment discovery is heavily dependent on the ability to evaluate new chemotherapeutic compounds that target this important neurofibromin growth regulatory pathway.

SUMMARY OF THE INVENTION

One aspect of the present invention encompasses a method for treating neurofibromatosis, the method comprising administering to a subject in need thereof an inhibitor of nucleophosmin (NPM).

Another aspect of the invention encompasses a method for treating neurofibromatosis, the method comprising administering to a subject in need thereof an inhibitor of Rac1.

Yet another aspect of the invention encompasses a cell comprising a vector. The vector generally comprises a reporter gene operably linked to a mTOR-responsive promoter.

Still another aspect of the invention encompasses a method of screening for a modulator of the neurofibromin pathway. The method comprises contacting a cell comprising a vector comprising a reporter gene operably linked to a mTOR-responsive promoter with a test compound. The level of a marker encoded by the reporter gene is measured, and the level of the marker compared to a control is indicative of a modulator of the neurofibromin pathway.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

DETAILED DESCRIPTION

Figure 1:
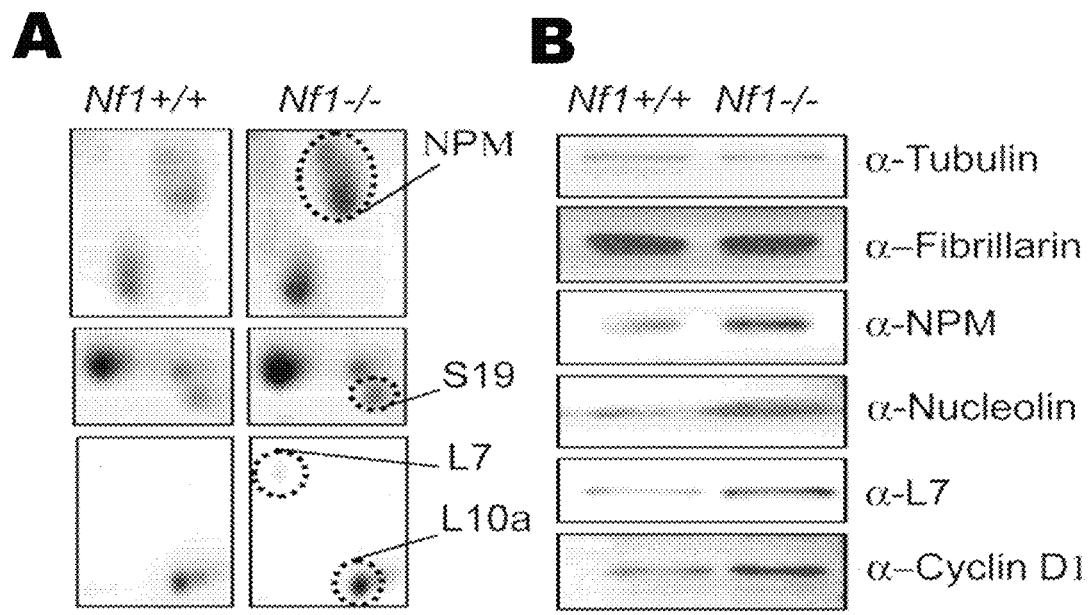
FIG. 1 depicts a series of images showing that loss of neurofibromin in primary astrocytes results in increased expression of proteins involved in ribosome biogenesis. (A) Two dimensional gel electrophoresis and MALDI-TOF analysis demonstrated that S19, L7, and L10a as well as nucleophosmin (NPM) were increased in neurofibromin $1^{-/-}$ (Nf1$^{-/-}$) astrocytes. (B) The two dimensional gel electrophoresis results were confirmed using Western blotting on wild-type (Nf1$^{+/+}$) and neurofibromin $1^{-/-}$ (Nf1$^{-/-}$) astrocytes.

Provided herein is a method for treating neurofibromatosis (NF1), which may be caused by a loss of neurofibromin protein function. The inventors have discovered that administering an inhibitor of either of the neurofibromin 1 pathway components nucleophosmin or Rac1 is capable of ameliorating the effects of loss of neurofibromin 1 function. The inventors have also discovered a method for identifying compounds that inhibit the neurofibromin pathway and neurofibromin 1 deficient cell growth.

I. Method for Treating Neurofibromatosis

Provided herein is a method for treating NF1 in a subject by administering a composition comprising an inhibitor of NPM and/or Rac1. As detailed above, generally speaking, loss of neurofibromin protein function results in NF1. Loss of neurofibromin protein function may be due to a non-functional neurofibromin 1 gene. For instance, a cell may contain one wild-type (functional) and one mutant (non-functional) copy of the neurofibromin 1 gene, leading to reduced neurofibromin 1 expression. This 50% reduction in neurofibromin 1 expression may be sufficient to result in the development of tumors. Alternatively, tumors may develop only after the wild-type copy of the neurofibromin 1 gene undergoes inactivation due to an acquired somatic mutation, leading to complete loss of neurofibromin 1 expression in those cells.

Disruption of both neurofibromin 1 alleles by mutation may occur in MPNSTs, juvenile chronic myeloid leukemia (JCML), pheochromocytoma, and dermal neurofibromas. Neurofibromin 1 inactivation and loss of neurofibromin 1 expression may be present in NF1-associated, but not sporadic, pilocytic astrocytoma. The neurofibromin 1 messenger RNA transcript may be expressed at variable levels in most tissues, but may primarily be detected in astrocytes, oligodendrocytes, neurons, Schwann cells, adrenal medulla, lymphocytes, and blood vessels.

(a) Nucleophosmin

NF1 may be treated by administering an inhibitor of nucleophosmin (NPM). An increase in mTOR activity, which may result from loss of neurofibromin function, may increase the translation of NPM. Inhibiting NPM function in a neurofibromin $1^{-/-}$ cell or in a subject with NF1 may restore cell proliferation to wild-type levels. NPM may be an mTOR effector important for regulating cell proliferation in neurofibromin $1^{-/-}$ cells. Inhibiting NPM function may have no measurable effect on the basal proliferation of wild-type astrocytes, underscoring its importance in neurofibromin 1 deficient cell proliferation.

In one embodiment, inhibitors of NPM may be used to treat NF1. The NPM inhibitor may be capable of substantially restoring neurofibromin $1^{-/-}$ cell growth to wild-type levels. NPM inhibitors are known in the art, and may be peptide or peptide derivative inhibitors, small molecular weight inhibitors, antibody inhibitors, or the like. For instance, in one embodiment, the NPM inhibitor may be NSC3848884.

(b) Rac1

NPM may be regulated by Rac1. Administering an inhibitor of Rac1 in an neurofibromin $1^{-/-}$ cell or to a subject with NF1 may greatly attenuate NPM expression and may treat NF1. Rac1 is a small GTPase, which may act downstream of mTOR and modulate actin stress fiber formation. Levels of active, GTP-bound Rac1 are elevated in neurofibromin $1^{-/-}$ mouse astrocytes. Rac1 hyperactivation is mediated by mTOR signaling in astrocytes. Rapamycin blocks Rac1 hyperactivation in neurofibromin $1^{-/-}$ astrocytes, indicating that Rac1 may act downstream of mTOR. Rac1 also regulates cell proliferation in a variety of cell types, and Rac1$^{-/-}$ mouse embryonic fibroblasts may exhibit both impaired migration and cell proliferation.

In one embodiment, inhibitors of Rac1 may also be used to treat NF1. The Rac1 inhibitor may be capable of substantially restoring neurofibromin $1^{-/-}$ cell growth to wild-type levels. Rac1 inhibitors are known in the art, and may be peptide or peptide derivative inhibitors, small molecular weight inhibitors, antibody inhibitors, or the like. For instance, in one embodiment, the Rac1 inhibitor may be selected from the group of inhibitors comprising NSC 23766, 553502, and EHT1864.

(c) Inhibitor Composition

Also provided herein is a composition comprising an inhibitor of NPM and/or Rac1. The composition may be in a pharmaceutically acceptable salt form. The term "pharmaceutically acceptable salt" refers to those salt forms which would be apparent to the pharmaceutical chemist, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients or their pharmaceutically acceptable salts in combination with pharmaceutically acceptable carriers.

Pharmaceutically acceptable salts of the active agents include, but are not limited to, salts formed with a variety of organic and inorganic acids such as hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid, sulfamic acid, glycolic acid, stearic acid, lactic acid, malic acid, pamoic acid, sulfanilic acid, 2-acetoxybenzoic acid, fumaric acid, toluenesulfonic acid, methanesulfonic acid, ethanedisulfonic acid, oxalic acid, isethonic acid, and include various other pharmaceutically acceptable salts, such as, e.g., nitrates, phosphates, borates, tartrates, citrates, succinates, benzoates, ascorbates, salicylates, and the like. Cations such as quaternary ammonium ions are contemplated as pharmaceutically acceptable counterions for anionic moieties. In addition, pharmaceutically acceptable salts of the compounds of the present invention may be formed with alkali metals such as sodium, potassium and lithium; alkaline earth metals such as calcium and magnesium; organic bases such as dicyclohexylamine, tributylamine, and pyridine; and amino acids such as arginine, lysine and the like.

The pharmaceutically acceptable salts may be synthesized by conventional chemical methods. Generally, the salts are prepared by reacting the free base or acid with stoichiometric amounts or with an excess of the desired salt-forming inorganic or organic acid or base, in a suitable solvent or solvent combination.

In general, the counterions of the salts may be determined by the reactants used to synthesized the compounds. There may be a mixture of counterions of the salts, depending on the reactants. For example, where NaI is added to facilitate the reaction the counterion may be a mixture of Cl and I counter anions. Furthermore preparatory HPLC may cause the original counterion to be exchanged by acetate anions when acetic acid is present in the eluent. The counterions of the salts may be exchanged to a different counterion. The counterions are preferably exchanged for a pharmaceutically acceptable counterion to form the salts described above. Procedures for exchanging counterions are described in WO 2002/042265, WO 2002/042276 and S. D. Clas, "Quaternized Colestipol, an improved bile salt adsorbent: In Vitro studies." Journal of Pharmaceutical Sciences, 80(2): 128-131 (1991), the contents of which are incorporated herein by reference. For clarity reasons, the counterions may not be explicitly shown in the chemical structures herein.

(d) Inhibitor Combinations

The composition may be administered in combination with a chemotherapeutic agent. The chemotherapeutic may be any pharmacological agent or compound.

The chemotherapeutic may be a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, I-asparaginase, interferons (preferably IFN-□), etoposide, and teniposide. Other proliferative cytotoxic agents are navelbene, CPT-11, anastrazole, letrazole, capecitabine, reloxafine, cyclophosphamide, ifosamide, and droloxafine. The cytotoxic agent may also be a combination of carboplatin and vincristine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; and Panda (1996) J. Biol. Chem 271:29807-29812.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used include, but are not limited to, hormones and steroids (including synthetic analogs): 17.alpha.-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, hlorotrianisene, hydroxyprogesterone, aminoglutethimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

In some embodiments, an inhibitor of NPM is administered in combination with an inhibitor of Rac1. In other embodiments, and inhibitor of NPM and/or and inhibitor of Rac1 is administered in combination with rapamycin.

(e) Formulations

The composition may further comprise one or more pharmaceutically acceptable additional ingredient(s) such as alum, stabilizers, antimicrobial agents, buffers, coloring agents, flavoring agents, adjuvants, and the like.

The composition may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

The composition may also be liquid formulations including, but not limited to, aqueous or oily suspensions, solutions, emulsions, syrups, and elixirs. The composition may also be formulated as a dry product for constitution with water or other suitable vehicle before use. Such liquid preparations may contain additives including, but not limited to, suspending agents, emulsifying agents, nonaqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

The composition may also be formulated as suppositories, which may contain suppository bases including, but not limited to, cocoa butter or glycerides. The composition may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. The composition may also be formulated transdermal formulations comprising aqueous or nonaqueous vehicles including, but not limited to, creams, ointments, lotions, pastes, medicated plaster, patch, or membrane.

The composition may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

The composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example).

The composition may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes may be used such as those described in U.S. Pat. No. 5,077,211, U.S. Pat. No. 4,621,023 or U.S. Pat. No. 4,508,703, which are incorporated herein by reference. A composition intended to target skin conditions can be administered before, during, or after exposure of the skin of the mammal to UV or agents causing oxidative damage. Other suitable formulations can employ niosomes. Niosomes are lipid vesicles similar to liposomes, with membranes consisting largely of non-ionic lipids, some forms of which are effective for transporting compounds across the stratum corneum.

(f) Administration

The composition for treating NF1 may be administered in a pharmaceutically effective amount. The composition may be administered simultaneously or metronomically with other anti-cancer treatments such as chemotherapy and radiation therapy. The term "simultaneous" or "simultaneously" as used herein, means that the other anti-cancer treatment and the composition is administered within 48 hours, 24 hours, 12 hours, 6 hours, 3 hours or less, of each other. The term "metronomically" as used herein means the administration of the composition at times different from the chemotherapy and at certain frequency relative to repeat administration and/or the chemotherapy regiment.

The composition may be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. The composition may also be administered in the form of an implant, which allows slow release of the composition as well as a slow controlled i.v. infusion.

(g) Dosage

A therapeutically effective amount of a composition required for use in therapy varies with the nature of the condition being treated, the length of time that activity is desired, and the age and the condition of the subject, and is ultimately determined by the attendant physician. The desired dose may be conveniently administered in a single dose, or as multiple doses administered at appropriate intervals, for example as one, two, three, four or more subdoses per day. Multiple doses often are desired, or required.

When given in combination with other therapeutics, the composition may be given at relatively lower dosages. In addition, the use of targeting agents may allow the necessary dosage to be relatively low. Certain compositions may be administered at relatively high dosages due to factors including, but not limited to, low toxicity, high clearance, low rates of cleavage of the tertiary amine. As a result, the dosage of a composition may be from about 1 ng/kg to about 200 mg/kg, about 1 µg/kg to about 100 mg/kg, or about 1 mg/kg to about 50 mg/kg. The dosage of a composition may be at any dosage including, but not limited to, about 1 µg/kg, 25 mg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

II. Vector

Another aspect of the invention is a vector that may be used in a method for screening for a modulator of mTOR, or alternatively, the neurofibromin pathway. Generally speaking, the vector may comprise an mTOR-responsive promoter and a reporter gene.

(a) mTOR-Responsive Promoter

Typically, the mTOR-responsive promoter is sensitive to changes in mTOR activity. For example, increased mTOR activity typically induces increased promoter activity of the mTOR-responsive promoter. Alternatively, decreased mTOR activity typically induces reduced promoter activity of the mTOR-responsive promoter. Consequently, the mTOR-responsive promoter is typically responsive to loss of neurofibromin 1 function (increased mTOR activity) and rapamycin inhibition (decreased mTOR activity).

The mTOR-responsive promoter may comprise a terminal oligopyrimidine (TOP) sequence. Usually, TOP sequences are comprised of between about 5 to about 15 pyrimidine nucleic acids. Non-limiting examples of TOP sequences include the sequences as set forth in Table 1.

TABLE 1

| ACCESSION NO | Sequence |
| --- | --- |
| L24371 | CUCUUUCC |
| M77232 | CCUCUUUUCC (SEQ ID NO: 1) |
| X67247 | CUCUUUCC |
| AB028894 | CCUUUCUCC |
| K02928 | CCUUUCU |

TABLE 1-continued

| ACCESSION NO | Sequence |
|---|---|
| D28350 | CUUUUUCCUCUCUUC (SEQ ID NO: 2) |

In one embodiment, the mTOR-responsive promoter may comprise the untranslated region (UTR) sequence of NPM, such as a portion of the 5'UTR. The 5'UTR may comprise a TOP sequence. Such a TOP sequence, for instance, may comprise the sequence as set forth in Table 2.

TABLE 2

| SEQ ID NO | Gene | Sequence |
|---|---|---|
| 3 | NPM1 | CUUUCCUUGGCGUGAUUCCGUCCUGCGCGUCUGU UCUGUGGAACAGGAGGCAGUUGUUUUCCGUCCGGCU UCUCCCACACCGAAGUGCGCGCCUCCACCUC |

(b) Reporter Gene

The mTOR-responsive promoter is generally operably linked to a reporter gene, which may encode a detectable marker. The marker may confer a phenotype on a host cell in which it is expressed to facilitate the screening or detection of cells in which the activity of the m-TOR-responsive promoter is modulated. Markers may include screening markers and/or selectable markers. Non-limiting examples of screening markers may include beta-galactosidase (β-gal), beta-glucuronidase (GUS), chloramphenicol acetyltransferase (CAT), green fluorescent protein (GFP), enhanced GFP (EGFP), yellow fluorescent protein (YFP), and luciferase. In one embodiment, the screening marker is luciferase, or another bioluminescent marker. Non-limiting examples of selectable markers may include ampicillin-resistance ($Amp^r$), tetracycline-resistance ($Tc^r$), bacterial kanamycin-resistance ($Kan^r$), zeocin resistance, the AURI-C which confers resistance to the antibiotic aureobasidin A, phosphinothricin-resistance, neomycin phosphotransferase gene (nptII), puromycin resistance or hygromycin-resistance.

(c) Neurofibromin Pathway

The neurofibromin pathway, as used herein, refers to biomolecules whose activity contributes to the pathogenesis of NF1 due to the loss of neurofibromin protein function. For instance, non-limiting examples of biomolecules in the neurofibromin pathway include mTOR, Rac1, NPM, S6, etc.

For example, loss of neurofibromin function in a cell may result in high levels of mammalian target of rapamycin (mTOR) pathway activation. In addition, gliomas from subjects with NF1 as well as from neurofibromin 1 genetically-engineered mice (GEM) typically have high levels of mTOR pathway activation. Loss of neurofibromin function in human MPNST cells may also correlate with high levels of mTOR activation. mTOR activation may be selectively inhibited by rapamycin.

mTOR is a protein serine-threonine kinase that integrates nutrient and mitogen signals to regulate cell growth and proliferation. mTOR may have downstream effectors, including two signaling pathways that may act in parallel to coordinate mRNA translation: the 70-kDa ribosomal protein S6 kinase (S6K) pathway and the eukaryotic translation initiation factor 4E (eIF4E)-binding protein 1 (4EBP1)/eIF4E pathway. Increased mTOR signaling may result in phosphorylation and activation of S6K, which may then phosphorylate and activate the S6 protein, a 40S ribosomal protein. Phosphorylated S6 may increase the translation of mRNAs containing a 5'-terminal oligopyrimidine domain (5'-TOP), many of which are ribosomal proteins, translation elongation factors and nucleolar chaperones. Hence, both S6k and the eIF4E pathway are in the neurofibromin pathway.

III. Cell

Yet another aspect of the invention encompasses a cell comprising the vector described in section II above. A cell of the invention may be used in a method for screening for a modulator of mTOR, or alternatively, the neurofibromin pathway. In some embodiments, the cell may further comprise a neurofibromin 1 gene. In certain embodiments, the cell may be an astrocyte, a glial cell, a glioma cell, a Schwann cell, or a malignant peripheral nerve sheath tumor cell (MPNST) or cell line, such as ST88-14 or NF90.8. The cell may lack neurofibromin 1 expression. The cell may be a mammalian cell. Non-limiting examples of mammalian cells include cells from laboratory animals (i.e. rats, mice, guinea pigs, etc.), non-human primates, and humans.

The cell may have reduced neurofibromin function, which may be due to a variety of reasons, including, but not limited to, a loss of function neurofibromin mutation or expression of a neurofibromin 1 small interfering RNA. The loss of function neurofibromin mutation may result in increased mTOR pathway signaling. The neurofibromin 1 mutant cell may be a primary culture cell, such as an astrocyte from a neurofibromin 1 conditional knockout mouse.

Furthermore, the cell may also express a marker that may be used to monitor cell proliferation. For instance, EGFP or another fluorescent or bioluminescent molecule independent from the marker incorporated into the vector may be used to monitor cell proliferation.

IV. Method for Screening

Still another aspect of the invention encompasses a method for screening for a modulator of mTOR. In one embodiment, the invention encompasses a method for screening for a modulator of the neurofibromin pathway. Generally speaking, the method comprises contacting a cell with a test compound, and detecting the ability of a test compound to affect the level of a marker that is operably linked to an mTOR-responsive promoter in the cell. A difference in the level of the marker in a cell contacted with a test compound compared to the level of the marker in a control cell may indicate that the test compound is capable of modulating mTOR, and therefore, in certain embodiments, capable of modulating the neurofibromin pathway. As used herein, "modulating" refers to increasing or decreasing the activity of a biomolecule. For instance, a test compound may modulate the neurofibromin pathway if the test compound increases or decreases the activity of mTOR, Akt, NPM, Rac1, S6K1, or S6. Generally speaking, the activity of a biomolecule may be increased by increasing the mRNA concentration of the biomolecule (i.e. increasing transcription or decreasing mRNA degradation), increasing the concentration of the biomolecule (i.e. increasing translation or decreasing degradation), or increasing the enzymatic activity of the biomolecule. Conversely, the activity of a biomolecule may be decreased by decreasing the mRNA concentration of the biomolecule (i.e. decreasing transcription or increasing mRNA degradation), decreasing the concentration of the biomolecule (i.e. decreasing translation or increasing degradation), or decreasing the enzymatic activity of the biomolecule.

In one embodiment, the method of the invention may be used to screen for compounds that modulate mTOR activity, but have no substantial effect on neurofibromin 1 deficient cell growth. In another embodiment, the method of the invention may be used to screen for compounds that do not substantially modulate mTOR activity, but substantially prevent cell growth. In yet another embodiment, the method of the invention may be used to screen for compounds that modulate mTOR activity and substantially prevent cell growth.

(a) Test Compound

The test compound may be present within a library (i.e., a collection of compounds). In one embodiment, the test compound may be encoded by DNA molecules within an expression library. In another embodiment, the test compound may be present in conditioned media or in cell extracts. In certain embodiments, the test compound may be known in the art as a "small molecule," which may have a molecular weight less than $10^5$ daltons, preferably less than $10^4$ daltons and still more preferably less than $10^3$ daltons. In some embodiments, the test compound may be provided as a member of a combinatorial library, which includes synthetic test compounds (e.g., peptides) prepared according to multiple predetermined chemical reactions. Those having ordinary skill in the art will appreciate that a diverse assortment of such libraries may be prepared according to established procedures, and members of a library of test compounds can be simultaneously or sequentially screened as described herein. For example, the library may be the NCI Structural Diversity Sets, Versions 1 or 2, the NCI Open Collection 1 or the ChemDiv Combilab or International Collections from the NCI.

A variety of formats may be used for screening, including in vitro, cell-based, in situ, and in vivo assays. Any suitable cells may be used. Generally speaking, the cells should be maintained in effective conditions, meaning conditions that support cell growth/proliferation if essentially no other regulatory compounds are present that would interfere with cell growth/proliferation. Effective conditions include, but are not limited to, appropriate medium, temperature, pH levels and oxygen conditions that permit cell growth. An appropriate medium is typically a solid or liquid medium comprising growth factors and carbon, nitrogen and phosphate sources, as well as appropriate salts, minerals, metals and other nutrients, such as vitamins, and includes an effective medium in which the cell can be cultured such that the cell can grow/proliferate. For example, for a mammalian cell, the media may comprise Dulbecco's modified Eagle's medium containing 10% fetal calf serum.

Cells may be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art.

Methods for contacting the cell with a test compound include, but are not limited to, mixing the test compound with the cell media, electroporation, microinjection, cellular expression (i.e., using an expression system including naked nucleic acid molecules, recombinant virus, retrovirus expression vectors and adenovirus expression), use of ion pairing test compounds and use of detergents for cell permeabilization.

A modulator of the neurofibromin pathway may have an $IC_{50}$ value between 1 mM and 1 µM. In a preferred embodiment, the IC50 value may be <1 µM.

(b) Detecting the Marker

The level of the marker may be detected using techniques standard in the art including, but not limited to, colorimetery, luminometery and fluorimetery. For example, the marker may be detected by using a fluorescent plate reader such as a FluoroSTAR dual fluorescence/luminescence plate reader (BMG LABTECH, Inc.). The level of the marker may also be detected may using pulse-labeling to determine whether a change in the level of the marker is due to a change in translation levels.

(c) Control

The control may be a cell that has wild-type neurofibromin function. The control may also be a cell contacted with a control agent, such as PBS, cell medium, or a known modulator of the neurofibromin pathway such as rapamycin.

The control may also be the level of cell growth, which may be indicative of the level of cytotoxicity of the test compound. A cytotoxic compound may reduce the amount of cell growth compared to no test compound. Cell growth may be determined in a number of methods, including use of a control vector. The control vector may comprise a growth marker. The growth marker may be a detectable label such as EGFP. The level of EGFP may be indicative of the level of cell growth and may be indicative of cell growth separate from mTOR signaling.

If contacting the cell with the test compound results in a reduction in the level of the mTOR-responsive marker compared to a no-test compound control, then the test compound may be an inhibitor of the neurofibromin pathway. If the test compound additionally does not reduce the level of the growth marker compared to a no-test compound control, then the test compound may not be cytotoxic. Such a test compound may be a selective inhibitor of the neurofibromin pathway.

If contacting the cell with the test compound results in an increase in the level of the mTOR-responsive marker compared to a no-test compound control, then the test compound may be an activator of the neurofibromin pathway.

(d) High-Throughput Screening

The test compound may be screened using high-throughput screening. For example, a 96- or 384-well plate format may be used. The test compound may be screened using a Beckman-Coulter Sagian Robotics Biomek FX Automated Workstation that is capable of detecting the mTOR-responsive marker. The high-throughput screening may comprise detecting the mTOR-responsive and the growth marker in a dual-labeled cell, enabling direct readout of fluorescence and bioluminescence non-destructively over the time-course of an experiment. The method may be capable of distinguishing cytotoxic versus cytostatic compounds throughout the course of a screen by multiple robotic readouts.

V. Mouse Comprising Vector of the Invention

A further aspect of the invention encompasses a mouse that comprises the vector detailed in section II above. Methods of engineering a mouse to comprise a nucleic acid vector are well known in the art. Such a mouse may be useful for screening for modulators of mTOR.

DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Administer" as used herein to describe the dosage of a compound, may mean a single dose or multiple doses of the compound.

"Combination with" as used herein to describe administration of a first treatment and an additional treatment means that the first treatment may be administered prior to, together with, or after the additional treatment, or a combination thereof.

"Effective amount" or "therapeutically effective amount" as used herein in reference to a compound, product, or composition as provided herein, may mean a sufficient amount of the compound, product or composition to provide the desired result. The exact amount required will vary depending on the particular compound, product or composition used, its mode of administration and the like. Thus, it is not always possible to specify an exact "effective amount." However, an appropriate effective amount may be determined by one of ordinary skill in the art informed by the instant disclosure using only routine experimentation.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. The promoter may comprise a T7, TP1, lactase, or metallothionein promoter.

"Peptide" or "polypeptide" as used herein may mean a linked sequence of amino acids which may be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

As used herein, "treating" means reversing, alleviating, inhibiting the progress of, or preventing neurofibromatosis, or one or more symptoms of such disorder or condition. The term "treatment", as used herein, unless otherwise indicated, refers to the act of treating as "treating" is defined immediately above.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome. Large numbers of suitable vectors and promoters are known to those of skill in the art and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223 3, pKK233 3, pDR540, pRIT5 (Pharmacia); Eukaryotic: pWLneo, pSV2cat, pOG44, pXT1, pSG (Stratagene) pSVK3, pBPV, pMSG, pSVL (Pharmacia).

EXAMPLES

The following examples illustrate various iterations of the invention.

Example 1

NF1-Deficient Cells and Tumors Exhibit High Levels of mTOR Pathway Activation

Figure 2:
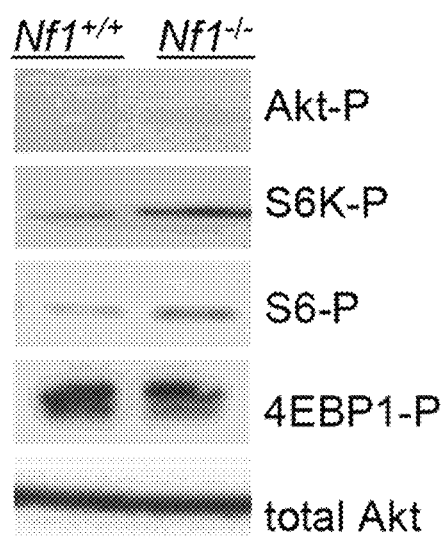
FIG. 2 depicts a series of images showing that loss of neurofibromin expression results in increased mTOR pathway activation. Using activation-specific (phospho) antibodies, neurofibromin $1^{-/-}$ (Nf1$^{-/-}$) astrocytes exhibit increased S6K1 and S6 activation relative to wildtype (Nf1$^{+/+}$) astrocytes, with no change in 4E-BP1 activation. A small increase in Akt activation was also observed.
Figure 3:
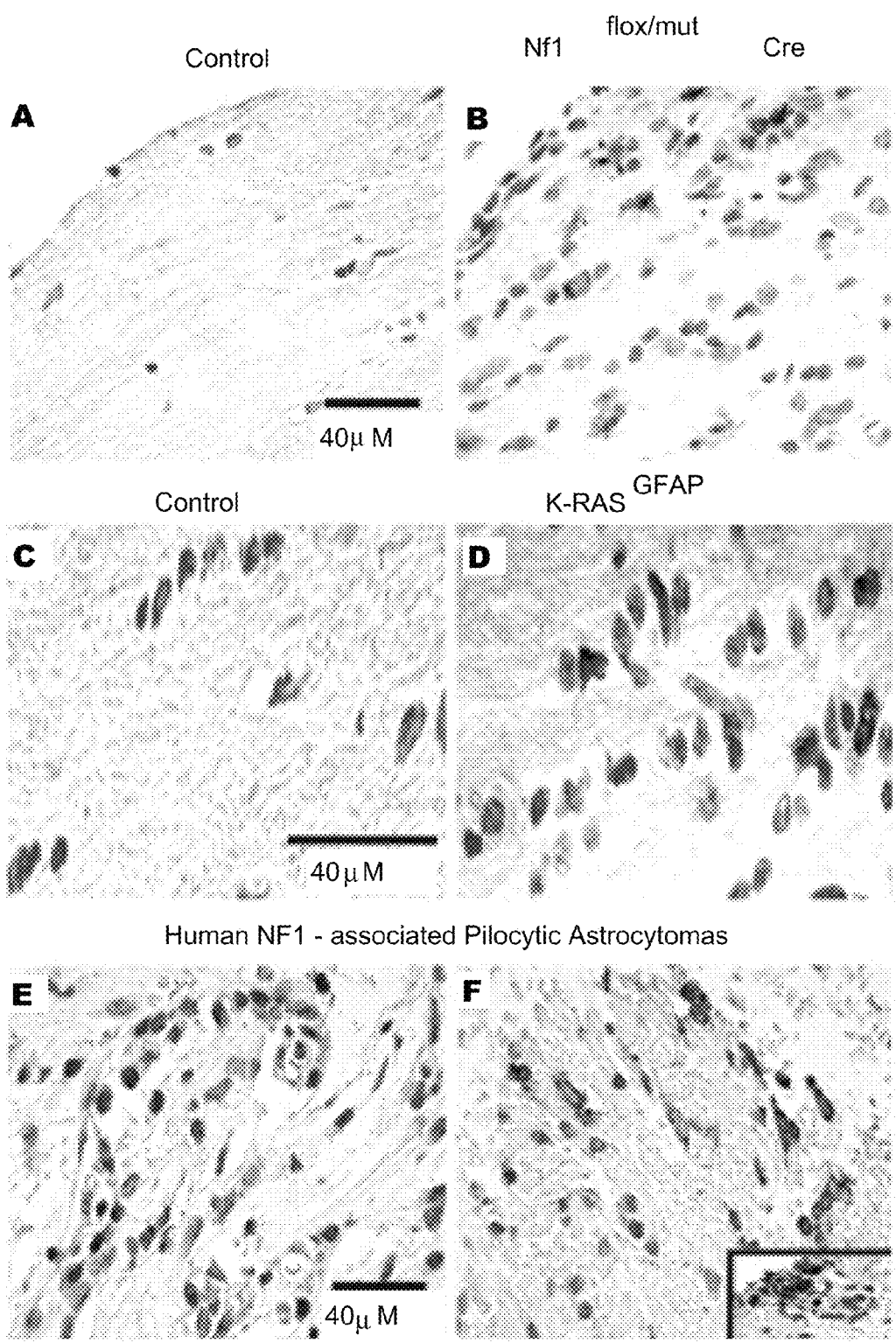
FIG. 3 depicts a series of micrographs showing that mTOR pathway hyperactivation is seen in NF1-associated mouse and human glioma. Increased S6 activation (phospho-S6 antibody) is observed in two models of Nf1 GEM optic glioma (panels B, D) relative to control brain (panels A, C) as well as in two representative human NF1-associated gliomas (panels E, F).

Two-dimensional gel proteomic profiling was used to identify signaling pathways deregulated by neurofibromin 1 inactivation in astrocytes. These experiments demonstrated increased expression of numerous members of the ribosomal synthesis pathway, including NPM, a key regulator of ribosome maturation and export (FIG. 1). Since ribosomal synthesis is modulated by the mTOR/S6K pathway, the activation status of select members of the mTOR pathway was analyzed, including S6K1, S6, and 4EP-B1 using activation-specific antibodies (FIG. 2). Increased activation of S6K1 and S6, but not 4E-BP1, in neurofibromin 1 deficient astrocytes was observed, suggesting that the S6K1/S6 arm of the mTOR pathway was hyperactivated. To provide an in vivo correlate for these in vitro findings, mTOR pathway activation was examined in optic glioma arising in neurofibromin 1 genetically-engineered mice (GEM) and in human NF1-associated pilocytic astrocytoma. S6 hyperactivation in both mouse and human optic glioma was observed by immunostaining with an activation-specific S6 phospho-antibody (FIG. 3). These results suggest that mTOR activation is maintained in NF1-associated tumors in vivo, and that mTOR inhibition may be a logical target for biologically-based therapy against tumors arising in NF1.

Example 2

Figure 4:
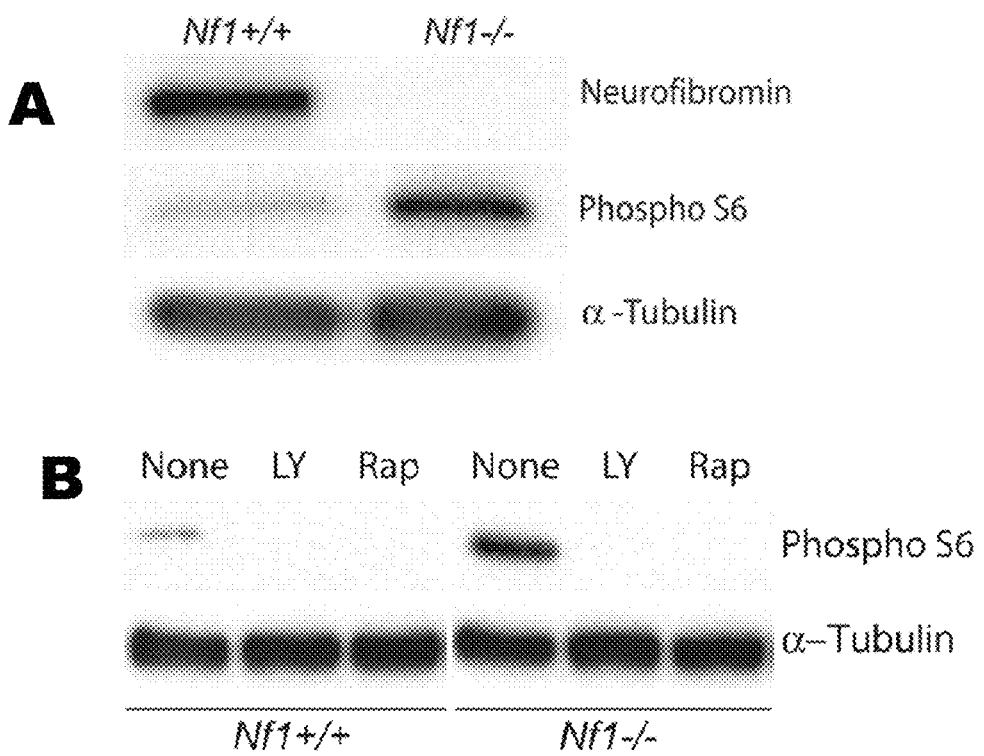
FIG. 4 depicts a series of images showing that neurofibromin 1 deficient astrocytes exhibit increased mTOR pathway activation, which is blocked by rapamycin. (A) Neurofibromin $1^{-/-}$ (Nf1$^{-/-}$) astrocytes exhibit high levels of activated S6 detected using phosphospecific antibodies compared to Nf1$^{+/+}$ wild-type astrocytes. (B) Treatment of neurofibromin $1^{-/-}$ (Nf1$^{-/-}$) astrocytes with rapamycin (Rap) or an inhibitor of PI-3K to block Akt activation (LY) eliminates the increased mTOR pathway activation (S6 phosphorylation).

Rapamycin Inhibition of mTOR Pathway Activation Blocks Neurofibromin 1 Deficient Cell Growth Pharmacologic inhibitors that block mTOR activation include rapamycin and related synthetic derivatives (e.g., RAD001, CCI-779). First, it was demonstrated that rapamycin inhibits mTOR pathway activation in neurofibromin 1 deficient astrocytes. In these experiments, complete inhibition of S6 activity was observed using phospho-specific antibodies after treatment with 1 nM rapamycin (FIG. 4).

Figure 5:
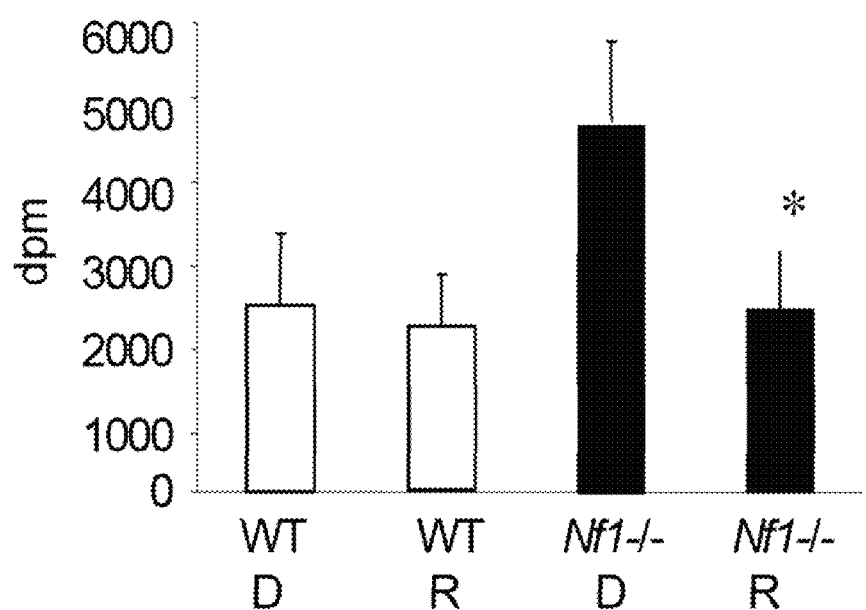
FIG. 5 depicts a graph showing that treatment of neurofibromin $1^{-/-}$ (Nf1$^{-/-}$) astrocytes with rapamycin inhibits cell proliferation. Nf1$^{+/+}$ (wild-type) or neurofibromin $1^{-/-}$ (Nf1$^{-/-}$) astrocytes were treated with vehicle (D) or rapamycin (R) and proliferation measured by thymidine incorporation. Rapamycin eliminated the neurofibromin 1$^{-/-}$ (Nf1$^{-/-}$) astrocyte growth advantage, but had no effect on wild-type astrocytes (P<0.01).
Figure 6:
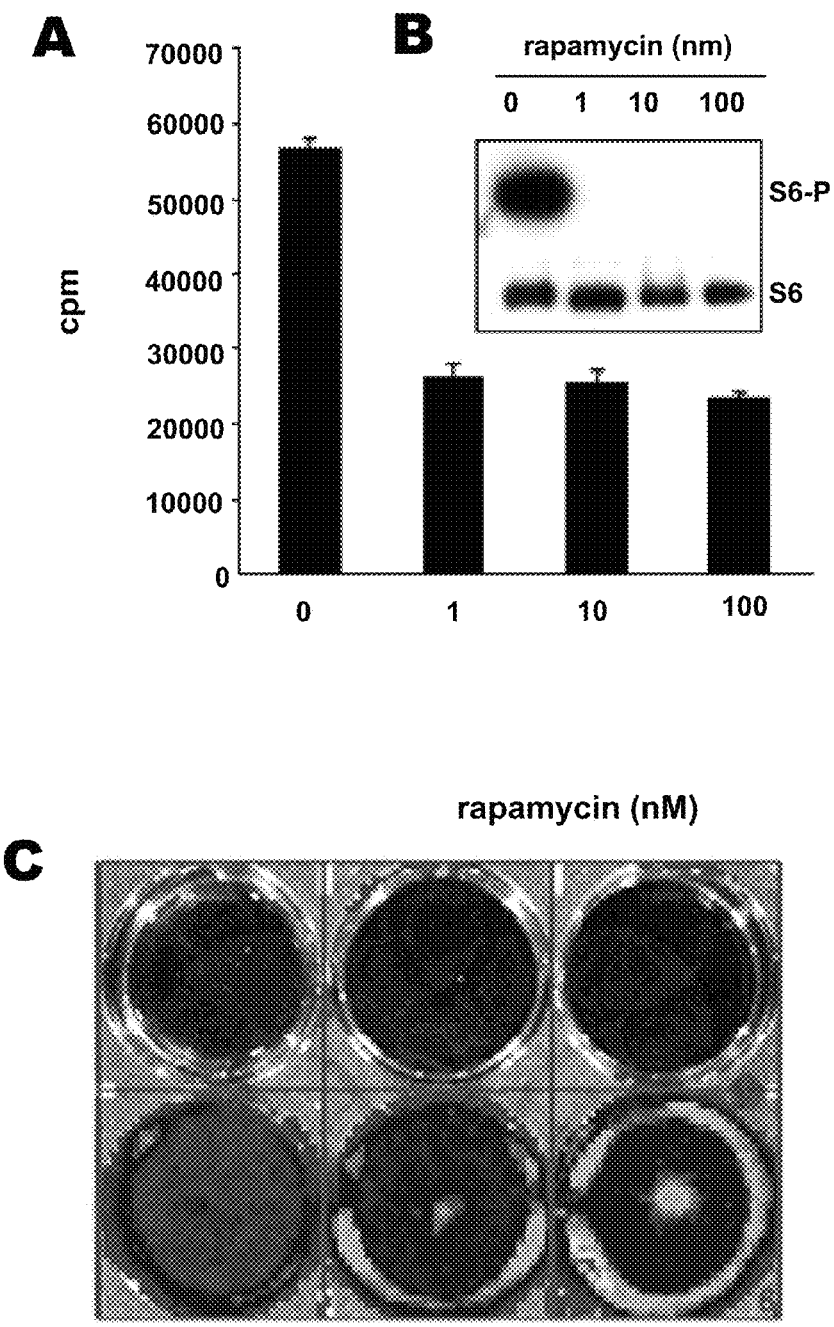
FIG. 6 depicts images and a graph showing that treatment of neurofibromin 1 deficient human MPNST cells with rapamycin results in attenuation of mTOR activation and reduced cell proliferation in vitro. (A) [$^3$H]-thymidine incorporation in vitro demonstrates reduced cell growth in response to low doses of rapamycin (1 nM). (B) Low doses of rapamycin inhibit the increased mTOR pathway activation (S6 phosphorylation; S6-P expression) observed in neurofibromin 1 deficient ST88-14 MPNST cells. (C) Luciferin bioluminescence demonstrates robust luciferase activity (red signal) in ST88-14-luc cells in vitro. The top three rows have no cells, while the bottom three rows contain $3\times10^5$, $6\times10^5$, and $9\times10^5$ ST88-14-luc cells. (D) $10^7$ neurofibromin 1 deficient MPNST cells (ST88-14-luc) were grown as a flank tumor in immunocompromised athymic nu/nu mice for 10 days. Following luciferin administration, in vivo bioluminescence imaging detects the growing tumor as denoted by the black arrow (red signal).
Figure 6D:
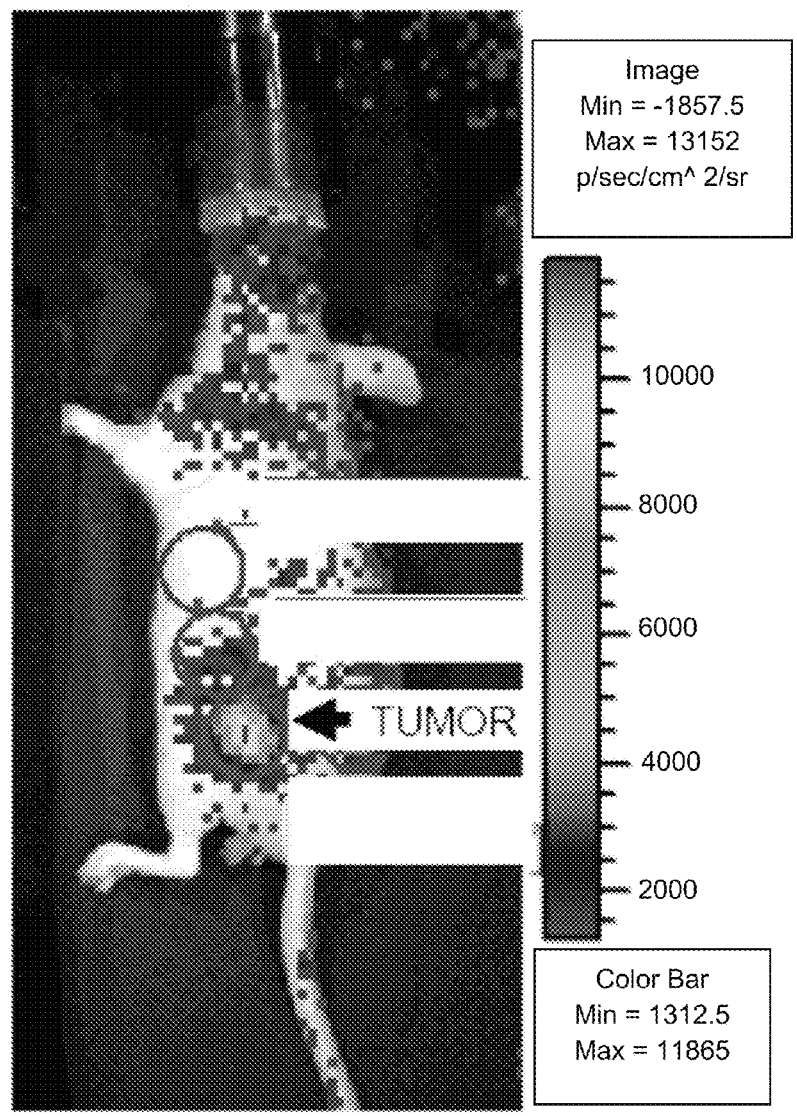

Second, this low dose of rapamycin was shown to completely inhibit the proliferative advantage of neurofibromin $1^{-/-}$ astrocytes in vitro without any effect on the growth of wild-type (neurofibromin $1^{+/+}$) astrocytes (FIG. 5). Finally, a human NF1-associated MPNST cell line (ST88-14) was engineered with a luciferase expression construct to allow for in vivo visualization and in vitro rapid analyses of cell growth (FIG. 6). Using the ST88-14-luc cell line, treatment with rapamycin effectively inhibited MPNST cell growth in vitro. Moreover, these engineered MPNST cell lines can be explanted into athymic nu/nu mice and tumor growth measured by bioluminescence imaging (FIG. 6d). Collectively, these experiments demonstrate that the growth of neurofibromin-deficient mouse and human cells can be inhibited with low doses of rapamycin.

Example 3

Neurofibromin Regulation of mTOR Signaling

Figure 7:
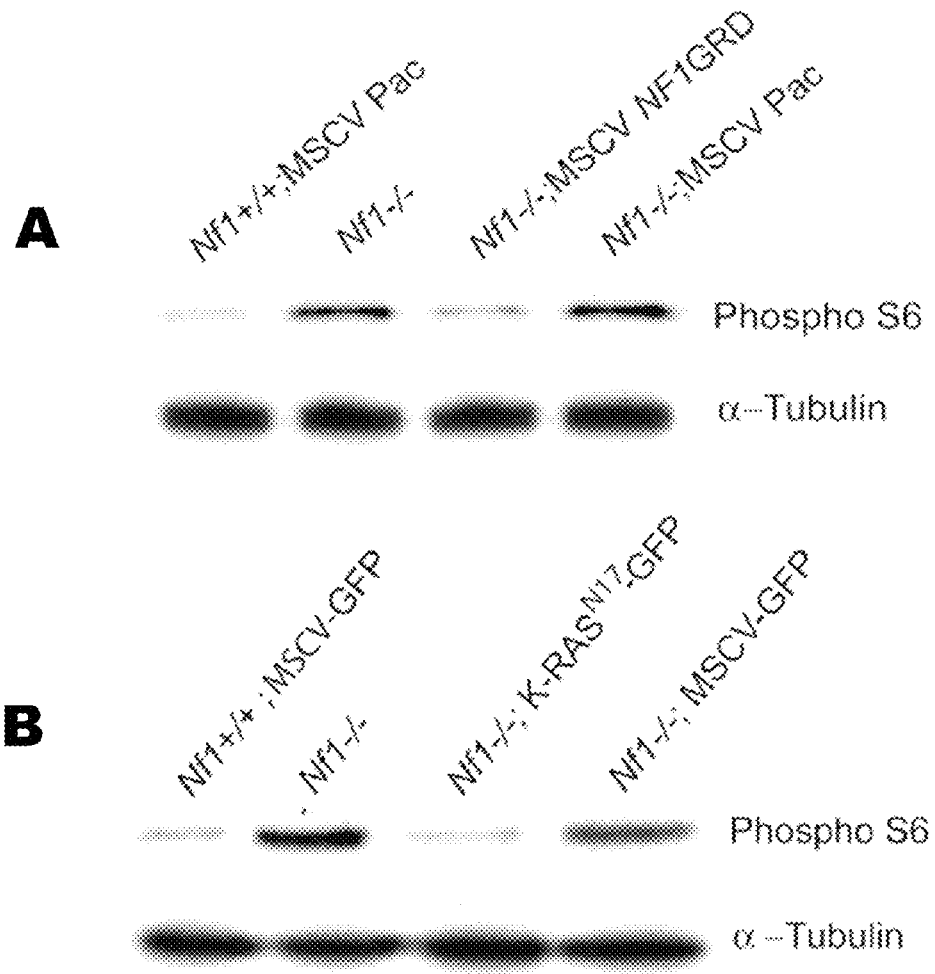
FIG. 7 depicts images showing that restoration of neurofibromin GAP activity or inhibition of KRAS activity blocks mTOR pathway activation in neurofibromin 1$^{-/-}$ (Nf1$^{-/-}$) astrocytes. (A) Neurofibromin 1$^{-/-}$ (Nf1$^{-/-}$) and Nf1$^{+/+}$ astrocytes were transduced with MSCV-NF1 GRD or MSCV-Pac (vector control). The increase in neurofibromin 1$^{-/-}$ (Nf1$^{-/-}$) astrocyte ribosomal S6 phosphorylation was reduced to wild-type levels by ectopic expression of the NF1 GRD, but not by transduction with MSCV-Pac. No change in S6 phosphorylation was observed in Nf1$^{+/+}$ astrocytes transduced with either MSCV-NF1 GRD or MSCV-Pac. (B) Similarly, transduction of the MSCV-dominant inhibitory K-RAS (K-RASN17) reduced S6 phosphorylation in neurofibromin 1$^{-/-}$ (Nf1$^{-/-}$) astrocytes to wild-type levels. Control MSCV (MSCV-GFP) had no effect on S6 hyperactivation in neurofibromin 1$^{-/-}$ (Nf1$^{-/-}$) astrocytes.

Evidence exists for direct activation of mTOR signaling by Akt as well as indirect activation of mTOR by Akt through the tuberous sclerosis complex (TSC)/Rheb pathway. Studies have shown that the mTOR activation resulting from neurofibromin loss in astrocytes can be reversed by restoring NF1-GAP activity (NF1 GRD), blocking K-RAS activity (K-RASN17), or inhibiting PI-3K activation of Akt. In these experiments, replacement of the GAP domain in neurofibromin 1 deficient astrocytes reduced S6 activation levels to normal (FIG. 7a). Similarly, the increased S6 activation in neurofibromin 1 deficient astrocytes was reversed upon the introduction of a dominant inhibitory K-RAS molecule (FIG. 7b) or inhibition of PI-3K using the LY294002 compound (FIG. 4b). Collectively, these results suggest that neurofibromin regulates mTOR signaling through RAS/Akt.

Figure 8:
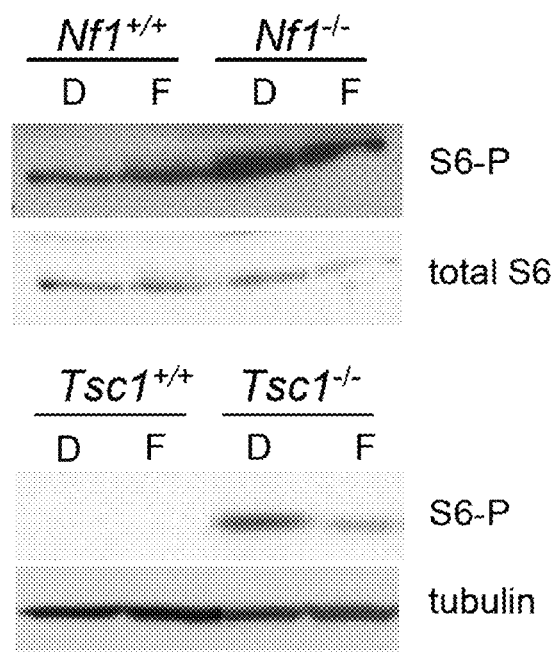
FIG. 8 depicts images showing that Rheb pharmacologic inhibition blocks mTOR pathway activation in Tsc1-deficient, but not neurofibromin 1 deficient, astrocytes. (TOP PANEL) Treatment of neurofibromin 1$^{-/-}$ (Nf1$^{-/-}$) astrocytes with FTI-276 (F) had no effect on S6 activity compared to control (D). (BOTTOM PANEL) In contrast, Rheb inhibition in Tsc1$^{-/-}$ astrocytes reduced S6 activation.

While one report found that neurofibromin 1 regulation of mTOR signaling involved the TSC/Rheb pathway, several lines of evidence using primary astrocytes argue against this interpretation. Previous studies on Tsc1-deficient astrocytes suggest that the phenotypes of these cells are dramatically different from neurofibromin 1 deficient astrocytes. First, neurofibromin 1 deficient, but not Tsc1-deficient, astrocytes exhibit increased cell growth under sub-confluent conditions. Second, Tsc1-deficient, but not neurofibromin 1 deficient, astrocytes exhibit dramatic increases in cell size. Third, while Tsc1-deficient astrocytes exhibit increased 4E-BP1 activation, no change in 4EBP1 activation is seen in neurofibromin 1 deficient astrocytes (FIG. 2). In each case, the abnormal $Tsc1^{-/-}$ and neurofibromin $1^{-/-}$ astrocyte phenotypes were reversed by mTOR inhibition (rapamycin treatment). To provide additional evidence for a TSC/Rheb-independent mechanism of mTOR activation in neurofibromin 1 deficient astrocytes, a compound (FTI-276) that has been shown to block Rheb activation was examined. In these experiments, it was found that FTI-276 effectively blocks S6 activation in Tsc1-deficient astrocytes; however Rheb inhibition in neurofibromin $1^{-/-}$ astrocytes did not reduce S6 hyperactivation (FIG. 8). These studies provide preliminary evidence for a TSC/Rheb-independent mechanism.

Example 4 mTOR-dependent Rac1 Hyperactivation in the Absence of Neurofibromin

Figure 9:
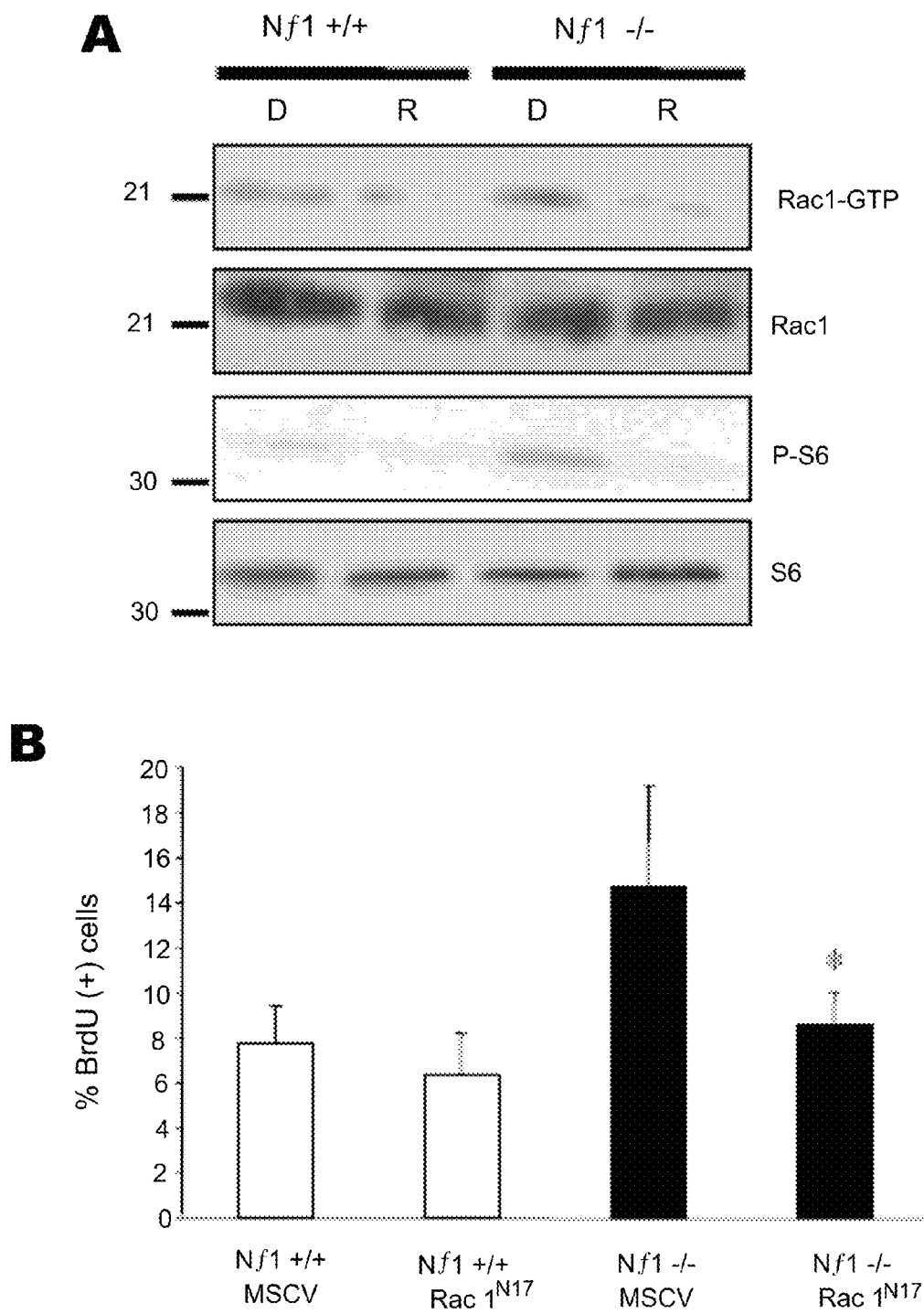
FIG. 9 depicts images and a graph showing that mTOR-dependent Rac1 hyperactivation is required for increased proliferation of neurofibromin 1$^{-/-}$ (Nf1$^{-/-}$) astrocytes. (A) GTP-bound Rac1 was immunoprecipitated from wild-type and Nf1$^{-/-}$ astrocytes treated with DMSO vehicle or 10 nM rapamycin using PAK1-PBD affinity chromatography. Equal protein loading was confirmed by immunoblotting for total Rac1 from a lysate aliquot prior to precipitation. (B) Expression of Rac1N17 in neurofibromin 1$^{-/-}$ (Nf1$^{-/-}$) astrocytes decreases cell proliferation, as determined by BrdU incorporation. *, p<0.05.

The small GTPase Rac1 has also been shown to act downstream of mTOR and modulate actin stress fiber formation. Previous studies have shown that neurofibromin $1^{-/-}$ astrocytes have increased levels of active, GTP-bound Rac1. To determine whether Rac1 hyperactivation was mediated by mTOR signaling in astrocytes, wild-type and neurofibromin $1^{-/-}$ astrocytes were treated with rapamycin (10 nM) and Rac1 activation was assayed. In these experiments, it was found that rapamycin blocked Rac1 hyperactivation in neurofibromin $1^{-/-}$ astrocytes (FIG. 9A), indicating that Rac1 acts downstream of mTOR. Rac1 has also been shown to regulate cell proliferation in a variety of cell types and $Rac1^{-/-}$ mouse embryonic fibroblasts exhibit both impaired migration and cell proliferation. To determine whether Rac1 regulates cell proliferation in neurofibromin $1^{-/-}$ astrocytes, Rac1N17 was expressed in wild-type and neurofibromin $1^{-/-}$ astrocytes and BrdU incorporation was examined. While expression of the dominant negative Rac1 had little effect on wild-type astrocytes, it restored proliferation of neurofibromin $1^{-/-}$ astrocytes to wild-type levels (FIG. 9B). Taken together, these data indicate that Rac1 is an important regulator of mTOR-dependent actin stress fiber formation and proliferation in astrocytes.

Example 5

Induction of NPM is Rapamycin-Sensitive

Figure 10:
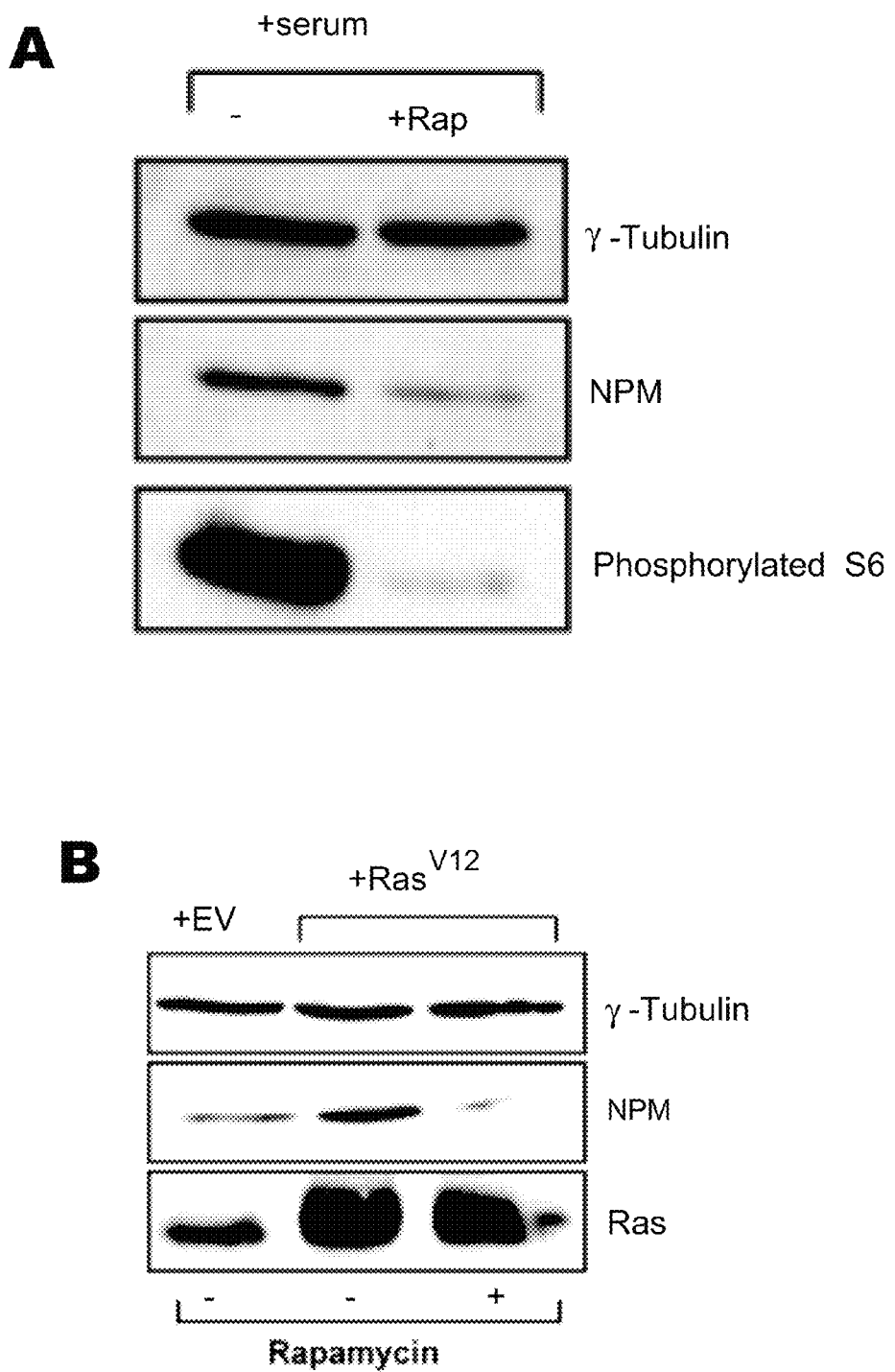
FIG. 10 depicts a series of images showing the effects of rapamycin on NPM expression. (A) Rapamycin (Rap, 100 nM) was added as indicated to asynchronous wild-type MEFs. Forty-eight hours after rapamycin treatment, cells were harvested and proteins were separated by SDS-PAGE and immunoblotted with antibodies specific for NPM, γ-tubulin and phospho-S6. (B) Wild-type MEFs were infected with retroviruses encoding β-galactosidase (EV) and RasV12. Rapamycin (100 nM) was added as indicated 24 hours post-infection. All samples were collected 48 hours post-infection and proteins were immunoblotted with antibodies against γ-tubulin, Ras and NPM.

Loss of neurofibromin has been shown to lead to dramatic (~5-fold) induction of NPM proteins. To determine whether NPM accumulation was dependent on hyperactivation of mTOR, it was tested whether rapamycin was able to block NPM induction in response to oncogenic RasV12. Primary mouse embryo fibroblasts (MEFs) were used in lieu of astrocytes due to their immediate availability for these experiments. Twenty-four hours post-infection, rapamycin was added to serum-stimulated or RasV12-infected mouse embryo fibroblasts and samples were collected 24 hours later. Analysis by Western blot demonstrated that NPM induction by serum or RasV12 was sensitive to rapamycin (Rap) treatments (FIG. 10).

Figure 11:
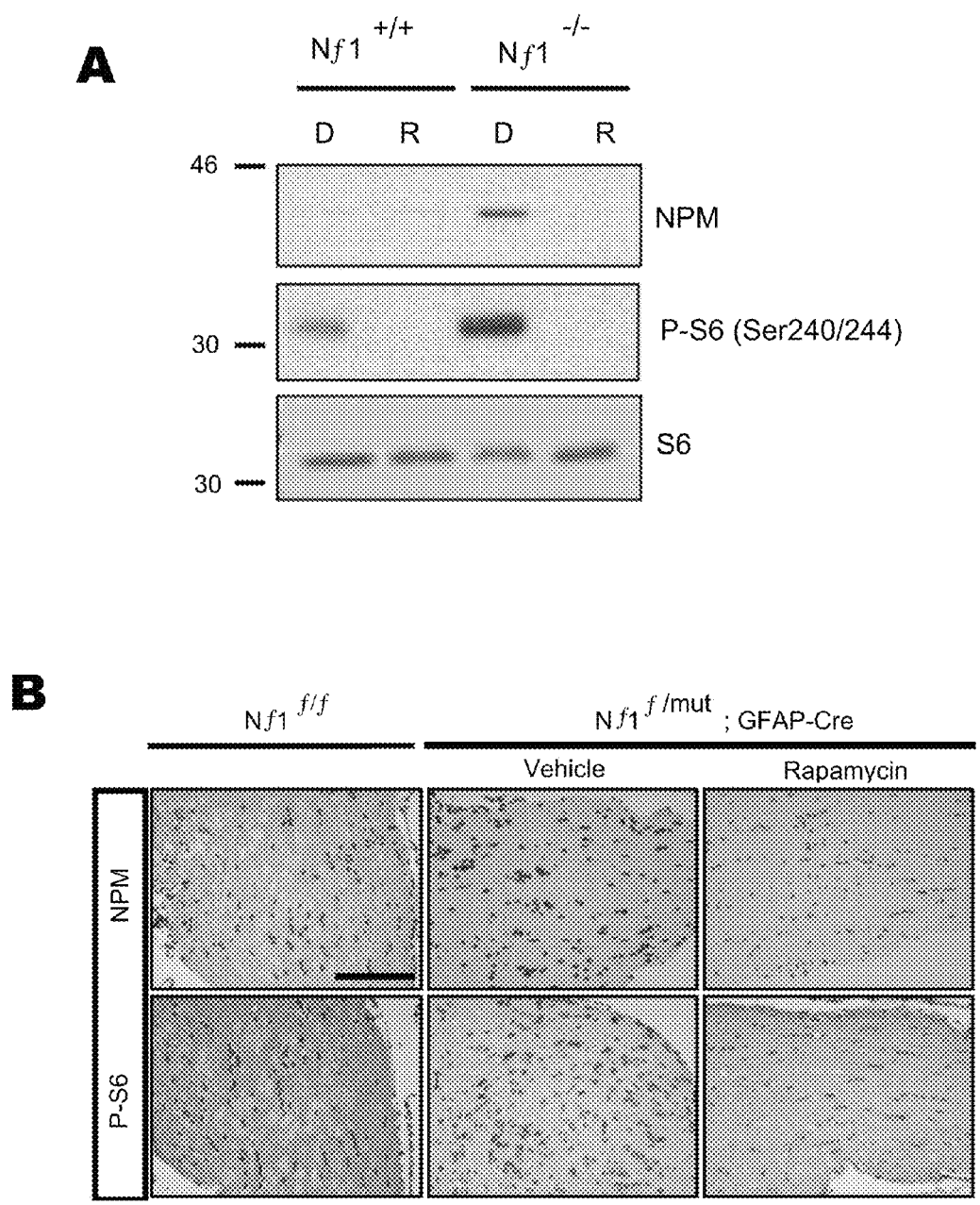
FIG. 11 depicts images and micrographs showing that nucleophosmin expression is regulated by mTOR signaling in vitro and in vivo. (A) Nucleophosmin (NPM) expression is increased in neurofibromin 1$^{-/-}$ (Nf1$^{-/-}$) astrocytes. Expression of NPM and P-S6 is inhibited by 10 nM rapamycin. Immunoblotting for total S6 demonstrates equal protein loading. (B) P-S6 and NPM are expressed at low levels in wild-type murine optic nerve (Nf1$^{f/f}$), but are dramatically increased in a murine model of optic glioma Nf1$^{f/mut}$; GFAP-Cre), as shown by immuno-histochemistry. Following rapamycin treatment in vivo, both NPM and P-S6 expression are decreased in the mouse optic gliomas. Scale bar=200 µm (10×).

In addition, it was also shown that the elevated NPM expression in neurofibromin 1 deficient astrocytes can be restored to wild-type levels with rapamycin treatment both in vitro and in vivo (FIG. 11).

Example 6

Nucleophosmin Induction in the Absence of Neurofibromin Requires Rac1 Signaling

Figure 12:
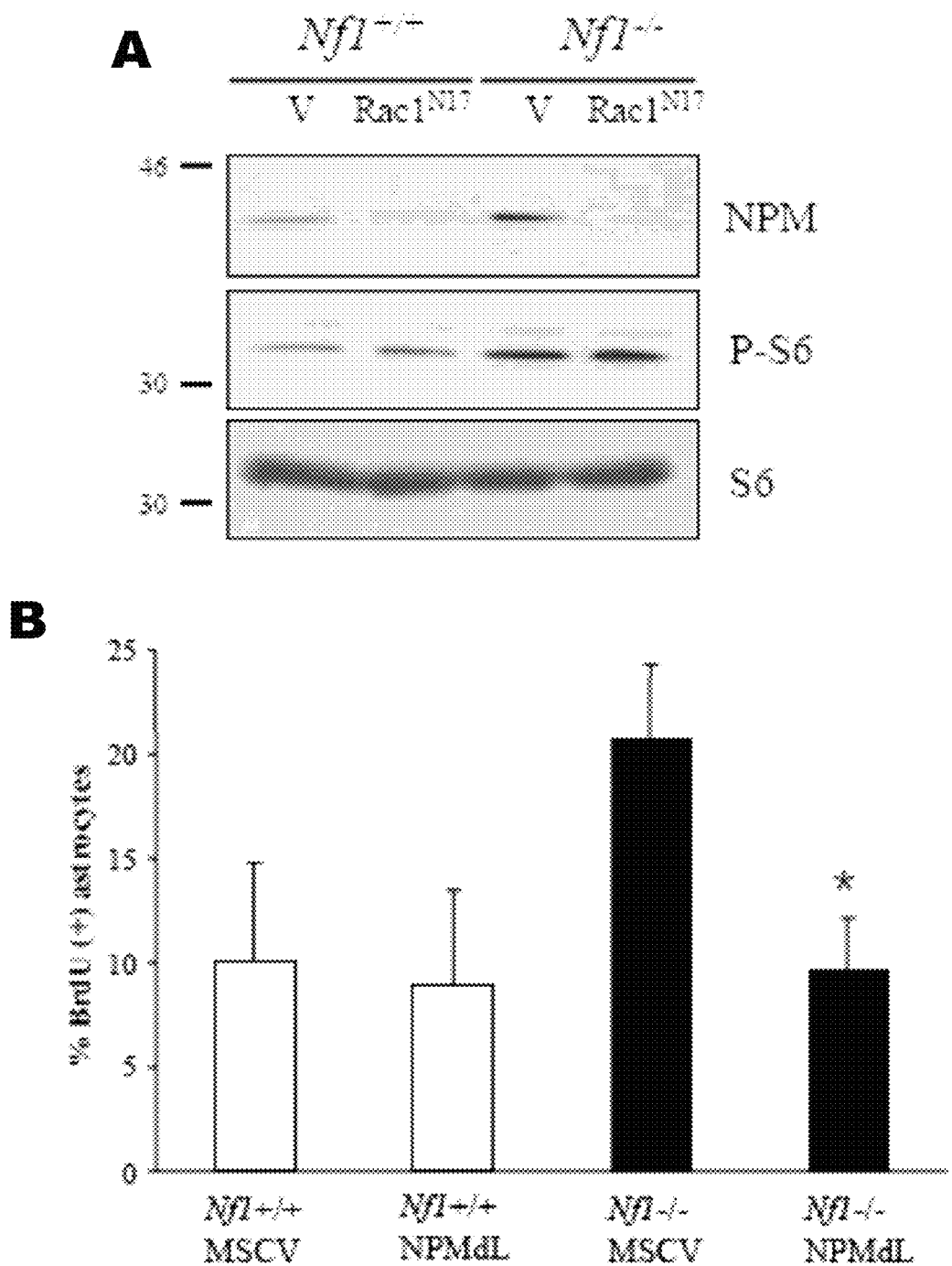
FIG. 12 depicts images and a graph showing the requirement of NPM expression and function for neurofibromin 1$^{-/-}$ (Nf1$^{-/-}$) astrocyte proliferation. (A) Expression of Rac1N17 in neurofibromin 1$^{-/-}$ (Nf1$^{-/-}$) astrocytes decreases NPM expression, but does not attenuate S6 phosphorylation. (B) Expression of the NPM shuttling mutant NPMdL in neurofibromin 1$^{-/-}$ (Nf1$^{-/-}$) astrocytes restores cell proliferation to wild-type levels. Inhibition of NPM shuttling function had no effect on proliferation in wildtype cells.

Because S6K/S6 and Rac1 were the mTOR effectors activated in neurofibromin $1^{-/-}$ astrocytes, it was determined whether either of these mTOR targets regulated NPM expression. When S6K was overexpressed in wild-type astrocytes, there was no change in NPM expression, despite an increase in S6 phosphorylation. This is in stark contrast to NPM regulation in primary MEFs where S6K is a potent inducer of NPM protein expression and highlights the potential differences in mTOR signaling mechanisms between fibroblasts and astrocytes. However, when Rac1N17 (dominant negative mutant) was expressed in neurofibromin $1^{-/-}$ astrocytes, NPM expression was greatly attenuated (FIG. 12A). No change in S6 or Akt activity was observed following Rac1N17 expression in neurofibromin $1^{-/-}$ or wild-type astrocytes, again demonstrating that Rac1 functions downstream of mTOR. Collectively, these results suggest that NPM functions downstream of mTOR and Rac1 via an S6K-independent mechanism in neurofibromin 1 deficient astrocytes.

Example 7

Nucleophosmin Mediates Cell Proliferation of Neurofibromin $1^{-/-}$ Astrocytes

To determine whether NPM regulates actin stress fiber formation in neurofibromin $1^{-/-}$ astrocytes, a novel NPM mutant was used to disrupt NPM function. One of the major roles of NPM is to mobilize ribosomes from the nucleolus to the cytosol. To disrupt this process, a mutant form of NPM (NPM double leucine mutant; NPMdL) that prevents NPM shuttling from the nucleolus to the cytoplasm was expressed. Previous studies have shown that this mutant behaves like a true dominant-negative protein, forming heterooligomers with endogenous NPM and blocking endogenous NPM from shuttling from the nucleus to the cytoplasm. The effect of inhibiting NPM function on neurofibromin $1^{-/-}$ astrocyte proliferation was examined. Similar to what was observed for rapamycin treatment and Rac1N17 expression, expression of the NPMdL mutant restored proliferation to wild-type levels (FIG. 12B). Together, these data indicate that NPM is a critical mTOR effector important for regulating cell proliferation in neurofibromin $1^{-/-}$ astrocytes. Additionally, the NPMdL mutant had no measurable effect on the basal proliferation of wild-type astrocytes (FIG. 12B), underscoring its importance in neurofibromin 1 deficient astrocyte proliferation.

A standard statistical analysis (e.g. student's T-test, standard deviations) was applied for the appropriate experiments in order to show statistical significance. A brief example summary of protein expression significance is listed in Table 1 (shown as ±SD for three independent experiments).

TABLE 1

| Protein | Proteomics | Western |
|---|---|---|
| NPM | 5.7 ± 0.75 | 6.4 ± 0.62 |
| rpL7 | 5.0 ± 0.96 | 5.0 ± 0.92 |
| rpL10a | 4.3 ± 1.31 | ND |
| Phospho-S6 | ND | 9.9 ± 1.74 |

Densitometry was performed on the indicated protein spots (Proteomics) or bands (Western blot) to determine the expression fold increase from neurofibromin 1 null cells over wild-type astrocytes. Standard deviations are presented from three independent experiments.

Example 8

Screening for Modulators of the Neurofibromin Pathway mTOR-Responsive Luciferase Reporter This example describes a process for generating a luciferase reporter that is sensitive to mTOR pathway activation resulting from neurofibromin loss. The 5'-untranslated region of NPM was cloned. This region was previously shown to contain a 5'-terminal oligopyrimidine (TOP) domain, making it sensitive to mTOR signals. Using this domain, a hybrid mRNA with the open reading frame of the firefly luciferase gene was generated.

Figure 13:
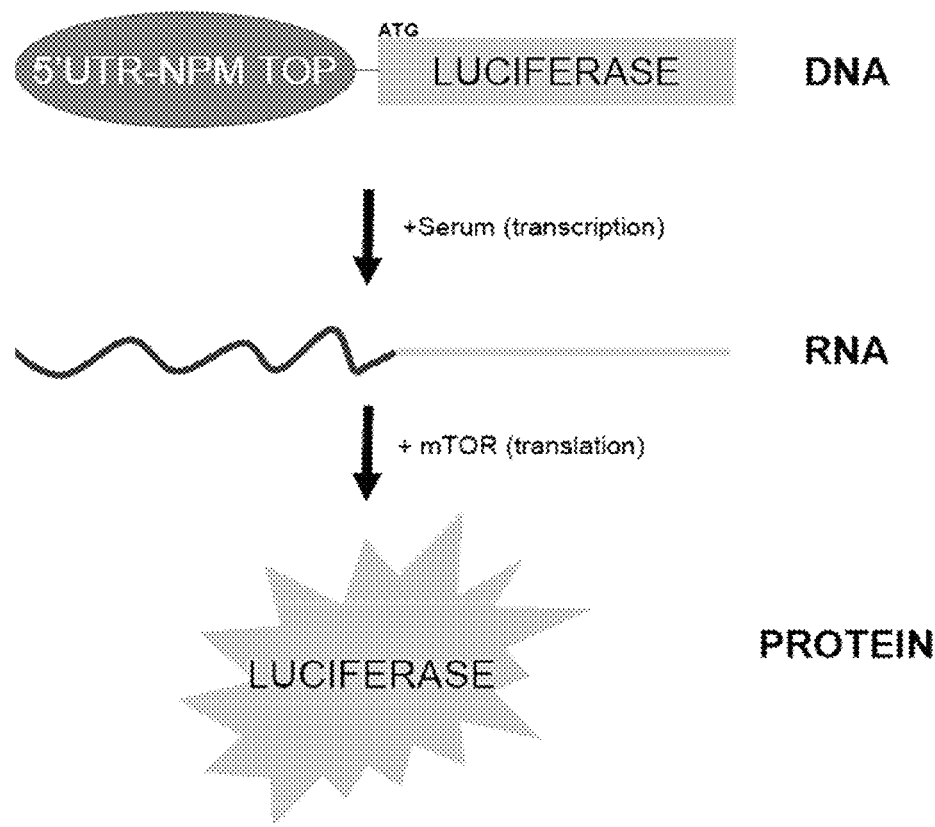
FIG. 13 depicts an illustration of the mTOR-responsive luciferase reporter. 5'-RACE analysis identified the 5'-untranslated region (UTR) of mouse NPM that is conserved in humans. (SEQ ID NO:4) The NPM 5'-UTR contains a putative terminal oligopyrimidine (TOP) sequence (underlined). The 5'-UTR of NPM was subcloned in front of the firefly luciferase expression cassette from the promoter-less pGL3 basic vector (Promega). Serum addition results in efficient transcription of the hybrid 5'-UTRNPM-TOP-luciferase gene through basal transcription sites within the 5'-UTR of NPM. The resulting RNA hybrid transcript is then placed under the control of regulatory sequences in the NPM 5'-UTR including the TOP sequence. Addition of hyper-active mTOR signals results in efficient translation of the hybrid transcript through sequences in the NPM TOP domain.

The hybrid mRNA was generated as follows (see schematic of FIG. 13). 5'-RACE was used to identify the 5'-untranslated region (UTR) of mouse NPM that is conserved in humans. The NPM 5'-UTR contains a putative terminal oligopyrimidine (TOP) sequence. In order to generate a hybrid reporter that is responsive to mTOR signals, the 5'-NPM TOP domain was fused to the extreme 5' end of the luciferase gene using unique KpnI and NcoI restriction sites in the pGL3-Basic reporter vector (Promega). The NcoI site enabled placement of the TOP domain immediately adjacent to the luciferase ATG start codon without adding any unwanted DNA sequences. This vector lacked an artificial promoter (e.g. CMV, MSCV) that could interfere with translation of resulting transcripts (due to addition of sequences to the 5'-UTR), and contained a polyA tail at the 3' end of the luciferase gene to increase RNA stability. In this regard, the 5'NPM TOP reporter should reflect regulation that is solely defined by the 5'-NPM TOP domain.

Responsiveness of the Reporter to Loss of Neurofibromin 1 Function

Figure 14:
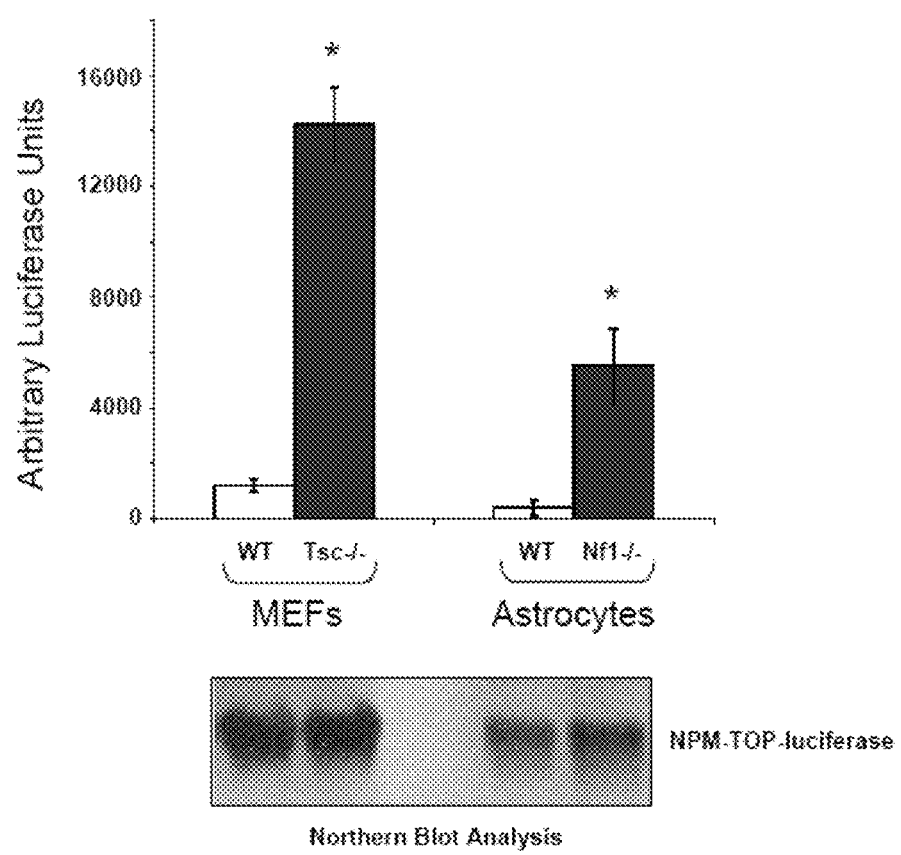
FIG. 14 depicts a graph and an image showing the validation of the 5'NPM-TOPluciferase reporter construct during mTOR hyperactivation. Primary mouse embryo fibroblasts ($1\times10^6$) derived from wild-type or Tsc$^{-/-}$ littermates were transduced with 2 µg of NPM-TOP-luciferase plasmid DNA and analyzed 48 hours later. Luciferin substrate was added and luminescence was measured in triplicate samples using standard luminometer techniques for luciferase detection. The identical assay was performed for primary mouse astrocytes ($1\times10^6$) derived from wild-type or neurofibromin 1$^{-/-}$ littermates. As a control for NPM-TOP-luciferase mRNA expression, Northern blot analysis was performed using a probe specific for the NPM-TOPluciferase mRNA. Equal mRNA ensures that increased luciferase expression was due to translation and not transcription. *=p<0.01.

Wild-type and neurofibromin 1 null astrocytes were transduced with the NPM-TOP-luciferase reporter. Cells were harvested and lysed 48 hours after transduction and assayed for luciferase activity by direct luminescence measurements. Northern blot analysis was performed using probes specific for luciferase in order to normalize for any alterations in the reporter's transcription rate to ensure that any differences in luciferase activity were a measure of translation of the reporter and not in its transcription. As anticipated, astrocytes lacking neurofibromin 1 displayed an approximate 12-fold increase in TOP-luciferase activity compared to wild-type cells (FIG. 14), indicating that this reporter is responsive to signals resulting from loss of neurofibromin.

Screening

Neurofibromin-deficient cell types would be used for these experiments. For the initial studies, human neurofibromin 1 deficient MPNST cells (ST88-14 and NF90.8) could be used as a primary filter for identifying compounds that inhibit mTOR pathway activation and cell growth. MPNST cells would be engineered to independently express the mTOR reporter construct as well as a separate transgene with enhanced green fluorescent protein (EGFP) expression. EGFP expression can be used to measure cell growth separately from mTOR activation. Compounds with activity in this initial screen may be validated using neurofibromin 1 deficient astrocytes derived from postnatal day 1-2 (PN1-2) pups. This secondary screen will employ standard proliferation assays, protein translation assessments, and measurements of mTOR pathway activation, as described herein.

The NPM 5'-TOP-luciferase reporter described above may be used to screen for novel mTOR pathway inhibitors. For transduction of the ST88-14-EGFP+MPNST cells, a puromycin cassette was placed in the NPM 5'-TOP-luciferase construct to allow for rapid selection of EGFP+ cells expressing the luciferase reporter. Luminescence and Western blot analysis will be performed using antibodies against luciferase to ensure proper luciferase expression in the transduced cells. This reporter construct worked in vitro and provided a sufficient signal to allow for the high throughput screen (see FIG. 14).

Two phases of screening will be employed. Phase I will be performed in 96-well plates with hand-held multipipetters and will be used to screen the 2000-compound NCI Structural Diversity Sets (Versions 1 and 2) obtained from the NCI Developmental Therapeutics Program. Results from Phase I will be applied to scale up in Phase II. Phase II will be performed with 384-well plates and our recently purchased Beckman-Coulter Sagian Robotics Biomek FX Automated Workstation will be used to screen the 90,000-compound NCI Open Collection 1.

Phase I

Figure 15:
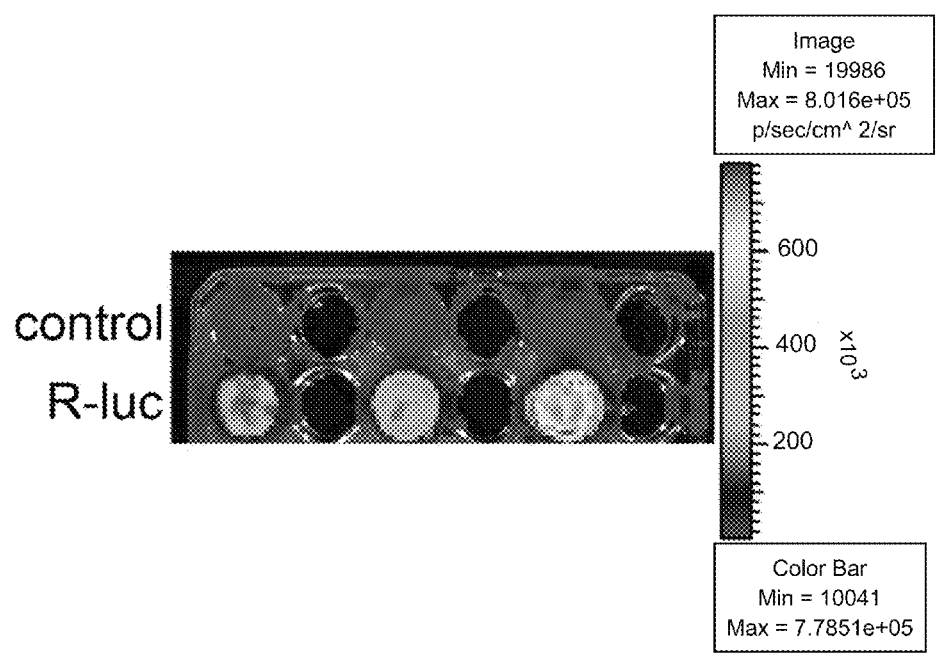
FIG. 15 depicts an image showing the luciferase reporter for proliferation of MPNST cells. ST88-14 cells transduced with control or Renilla luciferase (R-luc) vectors were seeded at $7.5\times10^4$, $1.5\times10^5$, and $2.5\times10^5$ cells respectively (left to right) overnight and were assayed the following day for luciferase activity.

This initial screen will be performed in duplicate 96-well plates. The duplication will be used to assay the effects of each compound on both neurofibromin 1 deficient MPNST proliferation and NPM 5'-TOP-luciferase expression in tandem to determine which compounds inhibit cell growth versus mTOR-driven luciferase expression. Each column on the plate will contain engineered MPNST cells and will be tested with 11 compounds per plate at 5 μM concentration. Cells will be incubated in test compound for 72 hours. At a rate of 220 compounds tested per day, the diversity set will be screened in 9 days. Each plate will have a control column with no compounds added, which allows for a first visual "hit"

scan. For growth measurements, EGFP fluorescence will be monitored using a fluorescent plate reader which will be optimized with control experiments prior to the actual screening assays. Fluorescence of each well will be measured with a highly sensitive FluoroSTAR dual fluorescence/luminescence plate reader (BMG LABTECH, Inc.) recently installed on a Sagian Robotics System platform. This will allow facile and sensitive determination of cell mass as a control R-luc function of compound identity on each plate using a standard cell proliferation assay. The advantage of this method is that transduced, dual-labeled MPNST cells will enable direct readout of fluorescence and bioluminescence non-destructively over the time-course of an experiment, thereby providing a method to distinguish cytotoxic versus cytostatic compounds throughout the course of a screen by multiple robotic readouts. Neurofibromin 1 deficient MPNST cells have been engineered to express Renilla luciferase (FIG. 15).

This method will be consistent with the bioluminescence technique for measuring NPM 5'-TOP-luciferase activity. After readout on the FluoroSTAR, data will be analyzed using a 96-well grid template available with the instrument software, which allows for fast and accurate determination of the emitted photons per well. The FluoroSTAR system software enables data to be directly transferred to Excel spreadsheets where values will be further analyzed. These positive "hits" in the first round will then be further analyzed, including tests for true positives, since a reduction in signal might result from fewer cells due to potential toxicity of any one compound within the Diversity Set.

Positive controls will be present in each plate in duplicate, represented by high-dose rapamycin (10 µM). Negative controls will be present as vehicle only wells containing the same volume and concentration of vehicle, but no compounds.

Phase II

Once modest throughput methods are validated in Phase I with the smaller compound library, the Sagian Robotics System will be implemented for screens of the 90,000-compound NCI Open Collection 1. The same cells, expression cassettes and methods will be used to screen larger diversity sets of compounds. As a conservative estimate, three-thousand compounds can be screened per day with the Sagian Robotics System and thus, the Open Collection 1 can be screened in 30 days. It is reasonable to anticipate that 6,000 compounds per day may be achievable, cutting screening time in half. Additional libraries from the NCI, such as the ChemDiv Combilab and International Collection, are available.

After the first round of screening, any hits obtained could be further validated in a second round of assays using neurofibromin $1^{-/-}$ and wild-type astrocytes. Astrocyte cultures could be chosen as a secondary screen because (a) they are primary cell cultures directly from neurofibromin 1 genetically-engineered mice, (b) they are genetically engineered to lack neurofibromin 1 expression, and (c) they represent a clinically-relevant cell type involved in the formation of NF1-associated brain tumors. MPNST cells have been adapted to growth in vitro for nearly two decades and likely contain a number of other genetic changes which may contribute to mTOR pathway hyper-activation. In this fashion, we will be able to evaluate compounds that specifically target mTOR activation that results from neurofibromin loss in cells that represent a primary cell type relevant to an important clinical manifestation of NF1. Lead compounds showing selectivity will then be further tested as a function of concentration to generate an $IC_{50}$. Only those compounds showing selective cytotoxicity with $IC_{50}$ values <1 µM will be further characterized. Desired compounds would be expected to selectively block the proliferation of neurofibromin $1^{-/-}$, but not wild-type astrocytes. Furthermore, these compounds could be studied for their ability to inhibit neurofibromin 1 deficient astrocyte proliferation, protein translation, NPM expression, ribosome nuclear export, and mTOR pathway activation.

Compounds would be expected to fall into three general categories: (1) those that prevent luciferase expression by inhibiting mTOR pathway activity but have no effect on neurofibromin 1 deficient cell growth, (2) those that prevent growth but not mTOR activity and (3) those that inhibit both mTOR pathway activity and cell growth. Compounds that fall into class 1 or 2 are unlikely to be valuable reagents for drug design, but class 1 compounds may provide important molecular probes to dissect the mTOR signaling pathway in mammalian cells. Class 2 compounds are likely to be cytotoxic or general inhibitors of proliferation (e.g. Cdk inhibitors, non-specific and general kinase domain inhibitors). Compounds that fall into the third group may be of great interest, especially those compounds with $IC_{50}$ values <1 µM and selectivity toward neurofibromin 1 deficient astrocytes.

The invention claimed is:

1. A method for treating neurofibromatosis, the method comprising administering to a subject in need thereof an inhibitor of nucleophosmin (NPM), wherein the inhibitor is NSC3848884 (2-(dimethylsulfamoylamino)-N-[(4-fluorophenyl)methylideneamino]acetamide).

2. The method of claim 1, further comprising administering an inhibitor of Rac1.

3. The method of claim 1, further comprising administering rapamycin.

4. A method for treating neurofibromatosis, the method comprising administering to a subject in need thereof an inhibitor of Rac1, wherein the inhibitor is NSC553502 (trimethylsilyl 2-methyl-2,3-bis(trimethylsilyloxy)propanoate) or EHT1864 (5-(5-(7-(Trifluoromethyl)quinolin-4-ylthio) pentyloxy)-2-(morpholinomethyl)-4H-pyran-4-one dihydrochloride).

5. The method of claim 4, further comprising administering an inhibitor of nucleophosmin (NPM).

6. The method of claim 4, further comprising administering rapamycin.

* * * * *

SEQUENCE LISTING

```
<160> NUMBER OF SEQ ID NOS: 4

<210> SEQ ID NO 1
<211> LENGTH: 10
<212> TYPE: RNA
<213> ORGANISM: Homo sapiens

<400> SEQUENCE: 1
ccucuuuucc                                                          10

<210> SEQ ID NO 2
<211> LENGTH: 15
<212> TYPE: RNA
<213> ORGANISM: Homo sapiens

<400> SEQUENCE: 2 cuuuuccuc ucuuc                                                     15
```

```
<210> SEQ ID NO 3
<211> LENGTH: 101
<212> TYPE: RNA
<213> ORGANISM: Homo sapiens

<400> SEQUENCE: 3 cuuccuugg cgugauuccg uccugcgcgu cuguucugug gaacaggagg caguuguuuu      60
ccguccggcu ucucccacac cgaagugcgc gccuccaccu c                       101

<210> SEQ ID NO 4
<211> LENGTH: 101
<212> TYPE: DNA
<213> ORGANISM: Mus musculus

<400> SEQUENCE: 4
ctttccttgg cgtgattccg tcctgcgcgt ctgttctgtg gaacaggagg cagttgtttt     60
ccgtccggct ctcccacac cgaagtgcgc gcctccacct c                        101
```